United States Patent
Lorenz et al.

(10) Patent No.: US 10,273,330 B2
(45) Date of Patent: Apr. 30, 2019

(54) HIGH-TOUGHNESS MATERIALS BASED ON UNSATURATED POLYESTERS

(71) Applicant: Fraunhofer-Gesellschaft zur Foerderung der angewandten Forschung e.V., Munich (DE)

(72) Inventors: Reinhard Lorenz, Steinfurt (DE); Monika Bauer, Konigs-Wusterhausen (DE); Sebastian Steffen, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 796 days.

(21) Appl. No.: 14/409,320

(22) PCT Filed: Jun. 19, 2013

(86) PCT No.: PCT/EP2013/062776
§ 371 (c)(1),
(2) Date: Dec. 18, 2014

(87) PCT Pub. No.: WO2013/190000
PCT Pub. Date: Dec. 27, 2013

(65) Prior Publication Data
US 2015/0175741 A1 Jun. 25, 2015

(30) Foreign Application Priority Data

Jun. 21, 2012 (DE) .................... 10 2012 210 483
Oct. 15, 2012 (DE) .................... 10 2012 109 803

(51) Int. Cl.
| | |
|---|---|
| *C10G 63/00* | (2006.01) |
| *C08G 63/00* | (2006.01) |
| *C08G 63/52* | (2006.01) |
| *C08G 63/676* | (2006.01) |
| *C09D 167/06* | (2006.01) |
| *C08L 67/06* | (2006.01) |
| *C07C 69/82* | (2006.01) |
| *C08L 67/00* | (2006.01) |

(52) U.S. Cl.
CPC ............ *C08G 63/00* (2013.01); *C07C 69/82* (2013.01); *C08G 63/52* (2013.01); *C08G 63/676* (2013.01); *C08L 67/00* (2013.01); *C08L 67/06* (2013.01); *C09D 167/06* (2013.01); *Y10T 428/249921* (2015.04); *Y10T 442/20* (2015.04)

(58) Field of Classification Search
CPC ...... C08G 63/00; C08G 63/52; C08G 63/676; C08L 67/06; C08L 67/00; C09D 167/06; C07C 69/82; Y10T 428/249921; Y10T 442/20
See application file for complete search history.

(56) References Cited

U.S. PATENT DOCUMENTS

| | | | | |
|---|---|---|---|---|
| 4,090,991 | A | 5/1978 | Fukusaki et al. | |
| 4,330,643 | A * | 5/1982 | Ogasawara | C08G 63/47 525/445 |
| 6,136,883 | A * | 10/2000 | Yang | B29C 70/34 427/220 |
| 6,489,406 | B1 * | 12/2002 | Mahbub | C08G 63/52 524/40 |
| 2011/0097530 | A1 * | 4/2011 | Gohil | B32B 27/08 428/36.92 |
| 2013/0288551 | A1 * | 10/2013 | Irnich | D06M 15/05 442/59 |

FOREIGN PATENT DOCUMENTS

| | | |
|---|---|---|
| CA | 2282412 A1 | 9/1998 |
| DE | 4406646 A1 | 9/1995 |
| GB | 722265 | 1/1955 |
| WO | 9846689 A1 | 10/1998 |

OTHER PUBLICATIONS

Mikhailova, Z. V. et al.: "Effect of Structure on the Physical and Mechanical Properties of Chemical-Resistant Unsaturated Polyester Resins", Polimery (Warsaw, Poland) (1979), 24(11-12), 407-409.

(Continued)

*Primary Examiner* — Cephia D Toomer
(74) *Attorney, Agent, or Firm* — Duane Morris LLP

(57) ABSTRACT

The present invention relates to unsaturated carboxylic acid ester obtained from or through the use of a source material defined below in formula (I):

$$A_{(0.9-1.2)}(B+C)_{(1.0)} \qquad (I)$$

wherein the figures set in parentheses indicate the molar proportion of source material A to the sum of source materials B and C, and wherein the following meanings apply:

A: unsaturated dicarboxylic acid,

B: a hard diol segment,

C: a soft diol segment selected from among compounds having a continuous chain between two hydroxyl groups, which have a length of 5 to 30 atoms, wherein the molar ratio of B:C is between 5:95 and 95:5. Furthermore, it relates to unsaturated polyester resin comprising said unsaturated carboxylic acid ester as defined above and a reactive diluents as well as molded articles, coatings, and surface textiles coated, saturated, laminated, and impregnated from or with a thermoset, which was obtained by hardening said unsaturated polyester resin.

16 Claims, No Drawings

(56) References Cited

OTHER PUBLICATIONS

Pandit, S. B. and Nadkarni, V. M., "Toughening of Unsaturated Polyesters by Reactive Liquid Polymers. 1. Synthesis and Characterization of the Modifiers", Ind. Eng. Chem. Res. (1993), 32, 3089-3099.
Pandit, S. B. and Nadkarni, V. M., "Toughening of Unsaturated Polyesters by Reactive Liquid Polymers. 2. Processibility and Mechanical Properties", Ind. Eng. Chem. Res. (1994), 33, 2778-2788.
Tsuneo, Imai: Nippon Fukugo Zairyo Gakkaishi (2007), 33(6), 227-231.

\* cited by examiner

HIGH-TOUGHNESS MATERIALS BASED ON UNSATURATED POLYESTERS

The present invention relates to unsaturated polyester resins having high fracture toughness, comprising a soft diol segment as well as a hard diol segment.

Fiber-reinforced unsaturated polyester resins are used extensively in the technical arena. Typical areas of application are in boot construction, the construction of tanks, containers, pipelines, and washers, in relining (sewer modernization), the production of panels as well as pressed components in accordance with the SMC process or the production of injection molded parts in accordance with the BMC process. The SMC and BMC process is used to produce parts for the electrical engineering industry (e.g. linear luminaire mounting brackets, switch cabinets, commutators), for the construction industry (e.g. basement window wells, pipe elements, and other construction elements) or for the automobile industry (e.g. body parts for cars and trucks, headlight reflectors, components for the interior of passenger train cars). Unsaturated polyester resins are also used to a limited extent for the production of rotary blades on wind turbines. In this application, they compete with epoxy resins, which have significantly higher fracture toughness and therefore enable a 'more slender' design comprising less mass due to the fact that they have to be designed less rigidly and greater deformations can be permitted, through which longer rotary blades (e.g. for offshore applications) are allowed.

Unreinforced applications of unsaturated polyester resins can be found, for example, in agglomerated marble for sanitary equipment or furniture, in paper laminates for furniture coating, in polymer concrete, in buttons for shirts and other clothing items, as well as in filler and repair compounds. Moreover, the diverse coating applications should be mentioned, which are also used under the designations of gel coat, topcoat, in-mold coat, and paint or anti-corrosive lining and provide surface finishing or surface protection in various ways.

An initial characterization of fracture toughness is possible from a fracture-mechanical perspective via a so-called $k_{1C}$ value (also called stress intensity factor in deformation mode I). With conventional UP resins common on the market, $k_{1C}$ values are measured between 0.35 and approx. 0.5, with epoxy resins for the mentioned wind turbines, values of approx. 0.8 are common. As an alternative to unsaturated polyesters and epoxy resins, the combination classes of vinyl ester and vinyl ester urethane resins (VE or VEU resins) are used in wind energy, which demonstrate $k_{1C}$ values between approx. 0.5 and 0.8.

DE 699 24 863 T2 reveals flexible unsaturated polyester resins that can be used at temperatures below 0° C. and are characterized by a very high weather resistance. These resins have molecular weights between 20,000 and 100,000 and are produced using (poly) glycol compounds having molecular weights between 300 and 12,000 and having an overall hydroxyl functionality of 2-4 per molecule. A ratio of 60-80 mole percent diols to 20-40 mole percent triols is preferred.

Toughness modifiers are compared with each other based on unsaturated polyester from 1 mol of MSA and 2 mol of PEG in the publication by S. B. Pandit and V. M. Nadkarni, "Toughening of unsaturated Polyesters by Reactive Liquid Polymers. 1. Synthesis and Characterization of the Modifiers", in Ind. Eng. Chem. Res. 1993, 32, 3089-3099 and "Toughening of unsaturated Polyesters by Reactive Liquid Polymers. 2. Processibility and mechanical Properties", in Ind. Eng. Chem. Res 1994, 33, 2778-2788 by the same authors.

DE 44 06 646 A1 describes products from trifunctional polypropylene oxides, which are terminally converted to so-called semi-esters with MSA without an additional polycondensation occurring. These products are used in vinyl ester and vinyl ester urethane resins as so-called thickening additives for MgO-based thickening, wherein they provide the COOH groups necessary for thickening that do not have VE or VU.

It is noted in the CAPLUS Abstract 1980:199205 regarding an article by Mikhaiolova, Z. V. et al. In Polimery (Warsaw, Poland) (1979), 24(11-12), 407-409 that the incorporation of polypropylene glycol into the chains of unsaturated polyesters from propoxylated bisphenol A and maleic anhydride leads to an improved elasticity of the resulting styrene-linked product, although the chemical resistance of the styrene-linked product decreases with increasing molecular weight beyond the examined molecular weight area of the polypropylene glycol used (500 to 4000). The abstract does not specify whether 1,2 or 1,3-Polypropylene glycol was used or a mixture of both.

Unsaturated polyester resins have a broad range of molar masses and lengths of network chains (meaning the network curve between two cross-linking points). This is due to the statistical nature of the unsaturated polyesters used, which normally have two dicarboxylic acids, one dicarboxylic acid capable of cross-linking (most often maleic and fumaric acid ester), and one dicarboxylic acid incapable of cross-linking (e.g. phthalic acid, isophthalic acid or adipic acid). Moreover, the length of the network curve of the radically formed chain (in the cross-linked product) is very short because there are only two to three units of reactive diluents (normally styrene) in the middle between two maleic or fumaric ester units. Thus, overall we obtain very heterogeneous networks with unsaturated polyesters, in which there are close-linked sections next to significantly less close-linked sections. The glass temperature of the cross-linked unsaturated polyester resins is essentially controlled through the ratio of dicarboxylic acid capable of cross-linking and that, which is not; this concept dominates in the chemistry of unsaturated polyesters. In addition, it is common to mix unsaturated polyesters having a high cross-linking density with those having a minimal cross-linking density so as to cover a larger interval in the case of thermal dimensional stability and glass temperature. In the process, the correlation generally applies—the higher the glass temperature, the less tough the material. It is understandable with this conventional concept of UP resin technology that areas having a higher cross-linking density are already being formed, which significantly limit the toughness of the UP resin-based materials.

The invention recommends avoiding this disadvantage. Surprisingly, this is possible through a fundamentally new approach, for which the chemical architecture of unsaturated polyester is modified such that the cross-linking points are spaced as evenly as possible. In doing so, the glass temperature can in a way that is new for UP resins, namely through the combination of two diols of a preferably equal chain length, which differ substantially in their chain rigidity and thus in their contribution to the glass temperature. For this purpose, for example, the substance class of diethoxylated or dipropoxylated bisphenols—hereinafter referred to as hard diol segments—as well as the substance class of propylene oxide or polypropylene glycols as well as ethylene oxide/propylene oxide co-glycols—hereinafter referred to as soft diol segments—is recommended. The glass temperature and toughness of the network can be set in a broad range via the mixture ratio of soft to hard diol segment.

Accordingly, unsaturated polyester resins are provided pursuant to the invention from or with the source materials defined below in formula (I):

$$A_{(0.9-1.2)}(B+C)_{(1.0)} \quad (I)$$

wherein the molar proportions of source material A to the sum of source materials B and C are indicated in parentheses.

Source material A in this formula is unsaturated dicarboxylic acid, which can be selected from among one or more carboxylic acids and/or their anhydrides. A specialist in the field of synthesis of unsaturated polyester resins is familiar with the source materials suitable in this regard. Fumaric acid, maleic acid, itaconic acid, and such, as well as the respective anhydrides are preferred.

Source material B is designated as a hard diol segment. It has (at least) two hydroxyl groups and a molecular structure having a continuous chain length of 5 to 30, preferably 5 to 25, and more preferably 10 to 25 atoms between both hydroxyl groups (or between respectively two of the hydroxyl groups should there be more than two hydroxyl groups), wherein these atoms are calculated as follows: the terminal hydroxyl groups are not included; however, the chain includes all chain links located between these hydroxyl groups, i.e. not merely the carbon atoms, but also N, O, and S atoms if they are present. Substituents or atoms from groups that branch off are not included. If there are ring structures in the chain, only those atoms of said ring structure are included, which contribute to the elongation of the chain. In this case, the shortest distance between the OH groups is selected for the calculation of the chain length. This will be 4 carbon atoms, for example, for one p-phenylene radical, 3 carbon atoms for one m-phenylene radical, and 2 carbon atoms for one o-phenylene radical. If a mixture of two or more substances is used as a hard diol segment, the aforementioned conditions must apply to the mixture. This means that not all of the substances as such have to comply with the conditions, even if this is beneficial, provided that the chain length lies within the aforementioned range on average with respect to the molar shares of the respective substances on source material B. In this regard, it is naturally beneficial if the chain lengths in such a mixture do not deviate from each other or only deviate slightly, e.g. in the range of ≤20%.

Hard diol segment B has a share of at least 40%, preferably at least 50%, and particularly preferably at least 70% atoms, which belong to a chain-rigid group with respect to the sum of the C, N, O, and S atoms of the molecule (i.e. not only with respect to the atoms of the chain), with the exception of the oxygen atoms of the terminal hydroxyl groups. Literature designates such groups as chain-rigid groups, for which monomer units are linked such that the entire group is rigid in the sense that it approximately or essentially has a (linear) rod structure. This is achieved by the fact that the atoms belonging to the backbone of the molecule in this area are linked to each other such that a rotation of two adjoining atoms is prevented either for chemical reasons (e.g. with a carbon atom having three binding partners) or for steric reasons, or that they symmetry of the group is such that rotation(s) around a single bond do not lead to a change of the axial direction of the group, such as is the case with the planar ring structures embedded in the backbone, the middle axis of which is in the axis of the respective rod structure and remains in said axis even in the case of a rotation around, e.g. single bonds to adjoining carbon atoms. A good representation of the concept of chain rigidity can be found in Angewandte Chemie 101(3), 362-410 (1989) by M. Ballauf. It should be noted in this regard that this concept is not only applicable on entire molecules, but rather even on parts thereof as well as on individual groupings/groups, which contribute to a rigidity of the molecule at the site of their incorporation for the stated reasons. With the aforementioned considerations in mind, particularly aromatic, aliphatic, and heterocyclic rings, including mono, bi, tri, and polycyclic compounds, amide, biuret, triazine, urea, thiourea, urethane and thiourethane groups, para, ortho, and meta-disubstituted $C_6$ aromatics, naphthyl groups as well as hetero aromatics are suited as chain-rigid groups for the hard diol segment capable of being used pursuant to the invention. This list is not necessarily complete—specialists are aware of additional chain-rigid groups.

Dialkoxylated, e.g. dipropoxylated or diethoxylated bisphenol A bodies are preferred as hard diol segment B; alternatively, e.g. other, likewise alkoxylated bisphenol bodies can be used, such as bisphenol F or bisphenol trimethylcyclohexane. The calculation of the chain length and the chain rigidity is shown based on bis-1,2-propoxylated bisphenol A—as the terminal hydroxyl groups are not included, said chain comprises two propoxy groups each having two C atoms in the chain and each having an oxygen atom as well as respectively four C atoms of phenylene groups and the C2 atom of the centric 2,2-substituted propane group, such that a chain length of 15 carbon or oxygen atoms emerges. Said molecule has two chain-rigid, conformationally less mobile phenylene groups and thus 12 atoms, which must be assigned to a chain-rigid structure. With a total number of 23 carbon and oxygen atoms of the molecule, 52% of the atoms contribute to the rigidity of the chain. It should be noted that the H atoms are neglected in this case due to their minimal mass.

In addition to the aforementioned chain-rigid, nitrogenous elements, the molecules may naturally contain other groups, e.g. those containing oxygen and sulfur, namely particularly even in the chain itself. In addition to ether groups, as they have the alkoxylated compounds, these may be, for example, ester groups.

The example of terephthalic acid esterified with glycol demonstrates where the limits of the invention are—the molecule has 12 chain links and a share of 6 chain-rigid carbon atoms on 16 C and O atoms and, therefore, does not fall under the invention. If peri-naphthalene dicarboxylic acid esterified with glycol is used instead, the chain has 11 chain links and a share of 12 chain-rigid carbon atoms on 22 carbon and oxygen atoms and can be used accordingly as a hard diol component pursuant to the invention. These esters containing hydroxyl groups can be viewed as prepolymers of polyester types (saturated); comparably, prepolymers of the polyamide or polyurea type can be used. Even mixtures are possible. The hard diol segment preferably bears no more than two hydroxyl groups.

Source material C is designated as soft diol segment. In contrast to hard diol segment B, this is a material having a flexible molecular structure. Like hard diol segment B, it has (at least) two hydroxyl groups and a molecular structure with a continuous chain length of 5 to 30, preferably 5 to 24 or to 25, and more preferably 10 to 24 or to 25 atoms between both hydroxyl groups (between respectively two of the hydroxyl groups if there happen to be more than two hydroxyl groups), wherein the same rules of calculation apply in this case as they are presented above for the hard diol segment. Soft diol segment C preferably has two hydroxyl groups. If a mixture of two or more substances is used as a soft diol segment, the aforementioned conditions must apply to the mixture as with the hard diol segment. This means that not all of the substances as such have to comply with the conditions, even if this is beneficial, provided that the chain length lies within the aforementioned range on average with respect to the molar shares of the respective substances on source material C. In this regard, it is naturally beneficial if the chain lengths in such a mixture do not deviate from each other or only deviate slightly, e.g. in the range of ≤20%

Soft diol segment C has a large share of unbranched and/or minimally-branched alkyl, polyether, polyester, or polycarbonate chains between both hydroxyl groups, which affect its softness. In contrast, the share of chain-rigid structures as defined above for the hard diol segment may be no more than 25%, preferably no more than 20%; the soft diol segment preferably does not contain any chain-rigid structures. The soft diol segment may be selected, e.g. from among α,ω-alkanediol, polypropylene glycols (including preferably tetramers to heptamers having a molar mass between 250 to 500, preferably to below 500, e.g. up to no more than approx. 450 g/mol, i.e. having no more than eight 1,2-Polypropylene glycol units according to a chain length between the hydroxyl groups of 24), polypropylene/polyethylene co-glycols, polytetrahydrofurans, polymers of 6-Caprolactone, 1,6-Hexane diol carbonates, $CO_2$-based polycarbonates, as well as additional chain-soft α,ω-hydroxy functional structures having a chain length of preferably 10-24 or 10-25 atoms, wherein said chain can have any "C-analogous" hetero atoms (selected from among O, S, N), provided they are not a part of a structure described above as chain-rigid, such as amide, biuret, triazine, urea, thiourea, urethane, and thiourethane groups. The last-mentioned groups, however, are not precluded if they do not make up—potentially with other structures—a greater share than 25%, preferably 20%, as defined above.

The (mol mass) sum of B+C is 1; the molar ratio of B:C is normally between 5:95 and 95:5, preferably between 10:90 and 90:10, more preferably between 30:70 and 70:30, and particularly preferably between 67:33 and 45:55. In the event that A=1, the number of carboxylic acid and hydroxyl groups in the source material is normally identical (namely insofar as all hard and soft diol segments B and C respectively bear precisely two hydroxyl groups). If A is not equal to 1, an acid deficit or excess acid emerges, which is knowingly selected and may be desired to obtain, e.g. radically reactive end groups with maleic and fumaric acid semi-esters.

The chain length of a hard and soft diol is at best identical; however, positive results are also achieved if the number of links of the continuous chain is between both (or with more than two OH groups in the molecule respectively between two of the) hydroxyl groups in the hard diol segment and the number of links of the continuous chain is between both (or with more than two OH groups in the molecule respectively between two of the) hydroxyl groups in the soft diol segment is in the ratio of between 1:2 and 2:1, preferably in the ratio of between 1:1.7 to 1.7:1.

In some cases, the source materials for the resins pursuant to the invention may have one or more saturated carboxylic acids having two carboxyl functions. They can be selected from among one or more carboxylic acids and/or their anhydrides. Examples are adipic acid or succinic acid and their anhydride. The expression "saturated carboxylic acid" also implies aromatic acids, for example, terephthalic acid, isophthalic acid, phthalic acid, and their anhydrides as they do not participate in the radical cross-linking reaction. Specialists in the field of synthesis of unsaturated polyester resins are aware of additional suitable source materials for this. In contrast, saturated or unsaturated monocarboxylic acids are only added in individual cases, e.g. for encapsulating the end group, i.e. for reducing terminal OH and COOH groups at the end of the chain. In this manner, for example, the water absorption of the hardened plastic can be gradually reduced.

The resin solution can be produced through heat, i.e. in the melt of the polyester, or cold in the reactive diluent. Compounds having at least one C=C double bond and potentially one aromatic ring, one cycloaliphatic ring, and one hetero ring, which can merge into a chain polymer under the influence of heat, light or ionizing radiation, are suitable as reactive diluents. The most important example for this is styrene. In addition, the use of a reactive diluent mixture can be beneficial to adapt the thickness of the cross-link and to increase the solubility of the unsaturated polyester in the reactive diluent, to improve the weather resistance and color fastness, as well as to accelerate or adapt the hardening. In addition to styrene, typical reactive diluents contain particularly alpha methylstyrene, other alkylated styrene derivatives, methyl methacrylate, tert-butyl acrylate, glycidyl methacrylate, maleic acid anhydride, trimethoxysilyl propyl methacrylate or triethoxysilyl propyl methacrylate. In principle, all monomers capable of a radical copolymerization with styrene are suitable. Silanes, such as trimethoxysilyl propyl methacrylate and triethoxysilyl propyl methacrylate are a particularly beneficial additive if the resin pursuant to the invention is intended to be used as a coating or impregnation of fiberglass due to the fact that it improves the adhesion of thermoset to fiberglass.

Resin, to which additives were provided (with or without reactive diluents), can be hardened as such to any molded articles or in the form of a coating on a substrate. In a specific embodiment, it acts to impregnate textile fabrics, such as woven and non-woven cloth or the like, the fibers of which can be comprised of glass, coal, aramid or another material. The lamination process, fiber spraying, the resin injection process (also called RTM), the winding process, the pultrusion process, the press process, and the injection molding process are used for the production of fiber-reinforced parts, namely respectively in combination with an impregnation step. Following a previous wetting step for fillers and pigments, the casting process as well as special impregnation processes (e.g. for paper) are primarily used for the production of unreinforced parts. Coatings are applied through immersion, filling, spraying, painting, squirting, by squeegee, and through injection, etc.

The unsaturated polyester resins pursuant to the invention into the materials pursuant to the invention can be hardened according to the state of the art. This primarily includes thermal (including ambient temperature) and radiation-chemical hardening. Specialists are aware of thermal and photochemical initiators required for this. In various cases, hardening is applied starting at room temperature, which is briefly designated at cold hardening. Cold hardening normally requires thermal initiators and so-called catalysts, which are known to specialists.

Prior to hardening, additives may be mixed into the resin. If there is reactive diluent, this should preferably occur after dissolving the resin components in the reactive diluents.

Specialists may select the additive(s) as needed. For example, all known toughening agents of an organic and inorganic nature (e.g. core shell particles, rubbers, waxes or silicones) can be added to the new unsaturated polyester resins as an additive in order to further increase the toughness of the resulting new materials. In many cases, even the known inorganic fillers, such as chalk, aluminum hydroxide (ATH), barite, quartz powder, and silicic acid are suitable for this. Adding these is beneficial in quantities less than 35 parts by weight with respect to 100 parts by weight of unsaturated polyester resin.

Moreover, additives known to specialists can be added when processing the new unsaturated polyester resins pursuant to the invention so as to optimize the processing and material properties. This includes, for example, skin enhancers for reducing the emission of styrene during processing, process additives for wetting and ventilating, thixotropic additives (for example, dispersed silicic acids), additional inhibitors for extending the storage period of resin and resin mixture, light stabilizers (for example, UV absorbers), fibers, fillers, dyes, pigments, and much more.

The present invention is particularly well suited for applications, in which the resin pursuant to the invention is intended to be used as a coating or in a fiber-reinforced form. Precisely in the case of applications in the construction industry and in the automobile industry, for example, impact and shatter resistance is required—and the present invention is capable of meeting these requirements. Glass temperatures capable of being reached pursuant to the invention (approx. 80 to 100° C.; the invention reaches 90 to 110° C.) are often necessary for outdoor applications as well. Therefore, particularly preferred applications for the invention are wind turbine blades and enclosures, boot walls and superstructures, containers, such as tanks, pipe elements, panels, pressed components for interior and exterior use, switch cabinets, construction elements for residential construction as well as parts for the transportation industry (e.g. for the interior of passenger train cars) as well as the automobile industry (e.g. body parts, headlight reflectors).

The following examples serve to provide additional understanding of the invention without limiting it.

RESIN EXAMPLE 1

Unsaturated polyester was produced in a polycondensation reaction. 1.36 mol of maleic acid anhydride, 0.41 mol of polypropylene glycol (molar mass of 425 g/mol), 0.95 mol of bis-propoxylated bisphenol A, and 150 ppm of hydroquinone were weighed into a 1-liter four-necked round-bottom flask and thermally subjected to a polycondensation reaction. The reaction was conducted without atmospheric oxygen. The resulting reaction water was separated through distillation. Polycondensation was conducted up to an acid value of 18.43 mg of KOH/g and a melt viscosity of 436 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

RESIN EXAMPLE 2

Unsaturated polyester was produced in a polycondensation reaction. 1.35 mol of maleic acid anhydride, 0.47 mol of polypropylene glycol (molar mass of 425 g/mol), 0.88 mol of bis-propoxylated bisphenol A, and 150 ppm of hydroquinone were weighed into a 1-liter four-necked round-bottom flask and thermally subjected to a polycondensation reaction. The reaction was conducted without atmospheric oxygen. The resulting reaction water was separated through distillation. Polycondensation was conducted up to an acid value of 23.81 mg of KOH/g and a melt viscosity of 238 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

RESIN EXAMPLE 3

Unsaturated polyester was produced in a polycondensation reaction. 2.69 mol of maleic acid anhydride, 1.08 mol of polypropylene glycol (molar mass of 425 g/mol), 1.61 mol of bis-propoxylated bisphenol A, and 150 ppm of hydroquinone were weighed into a 2-liter four-necked round-bottom flask and thermally subjected to a polycondensation reaction. The reaction was conducted without atmospheric oxygen. The resulting reaction water was separated through distillation. Polycondensation was conducted up to an acid value of 22.80 mg of KOH/g and a melt viscosity of 553 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

RESIN EXAMPLE 4

Unsaturated polyester was produced in a polycondensation reaction. 1.33 mol of maleic acid anhydride, 0.60 mol of polypropylene glycol (molar mass of 425 g/mol), 0.73 mol of bis-propoxylated bisphenol A, and 150 ppm of hydroquinone were weighed into a 1-liter four-necked round-bottom flask and thermally subjected to a polycondensation reaction. The reaction was conducted without atmospheric oxygen. The resulting reaction water was separated through distillation. Polycondensation was conducted up to an acid value of 24.50 mg of KOH/g and a melt viscosity of 122 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

RESIN EXAMPLE 5

Unsaturated polyester was produced in a polycondensation reaction. 2.76 mol of maleic acid anhydride, 1.38 mol of polypropylene glycol (molar mass of 425 g/mol), 1.38 mol of bis-propoxylated bisphenol A, and 150 ppm of hydroquinone were weighed into a 2-liter four-necked round-bottom flask and thermally subjected to a polycondensation reaction. The reaction was conducted without atmospheric oxygen. The resulting reaction water was separated through distillation. Polycondensation was conducted up to an acid value of 26.09 mg of KOH/g and a melt viscosity of 366 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

RESIN EXAMPLE 6

Unsaturated polyester was produced in a polycondensation reaction. 2.64 mol of maleic acid anhydride, 1.45 mol of polypropylene glycol (molar mass of 425 g/mol), 1.19 mol of bis-propoxylated bisphenol A, and 150 ppm of hydroquinone were weighed into a 2-liter four-necked round-bottom flask and thermally subjected to a polycondensation reaction. The reaction was conducted without atmospheric oxygen. The resulting reaction water was separated through distillation. Polycondensation was conducted up to an acid value of 19.00 mg of KOH/g and a melt viscosity of 346 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

RESIN EXAMPLE 7

Unsaturated polyester was produced in a polycondensation reaction. 2.62 mol of maleic acid anhydride, 1.57 mol of polypropylene glycol (molar mass of 425 g/mol), 1.05 mol of bis-propoxylated bisphenol A, and 150 ppm of hydroquinone were weighed into a 2-liter four-necked round-bottom flask and thermally subjected to a polycondensation reaction. The reaction was conducted without atmospheric oxygen. The resulting reaction water was separated through distillation. Polycondensation was conducted up to an acid value of 18.42 mg of KOH/g and a melt viscosity of 112 mPas (150° C. and 10000 1/s).

The resin was dissolved in 30 mass percent of styrene. The resin solution was hardened with 1.5 mass percent of tert-butyl perethylhexanoate for one hour at 80° C. and two hours at 120° C.

The glass transition temperature was determined via dynamic mechanical analysis (DMA) and fracture toughness was determined via optical crack tracing (OCT) (see Table 1).

TABLE 1

Fracture toughness and glass transition temperatures of the hardened resin examples

| Resin example | Fracture toughness $K_{1C}$ [MN/m$^{3/2}$] | Glass transition temperature [° C.] |
|---|---|---|
| 1 | 0.397 | 110 |
| 2 | 0.733 | 99 |
| 3 | 0.825 | 110 |
| 4 | 0.876 | 91 |
| 5 | 0.786 | 102 |
| 6 | 0.855 | 94 |
| 7 | 0.95 | 70 |

It should be noted that the presented examples demonstrate the ability to achieve high fracture toughness in combination with favorable glass transition temperatures without embodiments having to have been used, which reflect the expected optimum effect, due to the fact that hard and soft diol segments having identical or nearly identical chain lengths were used.

What is claimed is:

1. Unsaturated carboxylic acid ester obtained from or through the use of source or starting materials defined in formula (I):

$$A_{(0.9-1.2)}(B+C)_{(1.0)} \qquad (I)$$

wherein the figures in parentheses indicate the molar proportion of source material A to the sum of source materials B and C, and wherein A is an unsaturated dicarboxylic acid, B is a hard diol segment, wherein a proportion of at least 40% of the atoms of the hard diol segment belong to a chain-rigid group wherein said hard diol segment B is selected from the group consisting of compounds having at least two hydroxyl groups and a continuous chain between both hydroxyl groups which has a length of 5 to 30 carbon atoms, and wherein said continuous chain comprises carbon atoms, and optionally comprises at least one of N, O and S atoms, and C is a soft diol segment selected from the group consisting of compounds having a continuous chain between two hydroxyl groups, said chain having a length of 10 to 25 atoms, wherein in said soft diol segment that proportion which belongs to a chain-rigid group makes up no more than 25% of the atoms of the compound, in each case related to the number of C atoms and, if present, N, O and S atoms, between the hydroxyl groups in the compound with the exception of the oxygen atoms of the terminal hydroxyl groups;

wherein the molar ratio of B to C is between 5:95 and 95:5; and wherein the number of atoms of said continuous chain between both hydroxyl groups in said hard diol segment and the number of atoms of said continuous chain between both hydroxyl groups in said soft diol segment has a ratio of between 1:2 and 2:1.

2. Unsaturated carboxylic acid ester according to claim 1, wherein said soft diol segment does not comprise more than two hydroxyl groups.

3. Unsaturated carboxylic acid ester according to claim 1, wherein the length of a continuous chain between two hydroxyl groups in said hard diol segment and/or the length of said continuous chain between two hydroxyl groups in said soft diol segment is 10 to 24 atoms.

4. Unsaturated carboxylic acid ester according to claim 1, wherein the number of links of said continuous chain between both hydroxyl groups in said hard diol segment and the number of links of said continuous chain between both hydroxyl groups in said soft diol segment has a ratio of between 1:1.7 to 1.7:1.

5. Unsaturated carboxylic acid ester according to claim 1, wherein in the hard diol segment B, a proportion of at least 50% of the atoms of the compound belongs to a chain-rigid group, and/or wherein in the soft diol segment, less than 15% of the atoms belong to a chain-rigid group.

6. Unsaturated carboxylic acid ester according to claim 1, wherein said hard diol segment B is selected from the group consisting of dialkoxylated bisphenol A bodies, bisphenol F bodies, and bisphenol trimethylcyclohexane bodies.

7. Unsaturated carboxylic acid ester according to claim 6, wherein said soft diol segment C is selected from the group consisting of polypropylene glycols, polypropylene/polyethylene co-glycols, polytetrahydrofurans, polymers of 6-caprolactone, 1,6-hexandiolcarbonates, $CO_2$-based polycarbonates as well as α,ω-hydroxy functional compounds having a chain length of 10-25 atoms, which are carbon atoms.

8. Unsaturated polyester resin, comprising an unsaturated carboxylic acid ester according to claim 1, and at least one compound having at least one C=C double bond.

9. Unsaturated polyester resin according to claim 8, further comprising one or more additives selected from the group consisting of toughening agents, reinforcing fibers, fillers, pigments, dyes, and process additives.

10. Unsaturated polyester resin according to claim 9, wherein the toughening agents are selected from the group consisting of core-shell particles, rubbers, waxes, and silicones.

11. Molded article comprising a thermoset, which was obtained by hardening said polyester resin according to claim 8.

12. Molded article, comprising a textile fabric, which is coated, soaked, impregnated or laminated with a thermoset, wherein said thermoset was obtained by hardening said polyester resin according to claim 8.

13. Unsaturated carboxylic acid ester according to claim 1, wherein in the hard diol segment B, a proportion of at least 75% the atoms of the compound belong to a chain-rigid group, and/or wherein in the soft diol segment, less than 15% of the atoms belong to a chain-rigid group.

14. Unsaturated carboxylic acid ester according to claim 5, wherein no chain-rigid groups are present in the soft diol segment.

15. Unsaturated carboxylic acid ester according to claim 7, wherein the carbon atom chain is interrupted by O, S, NH or NR, and wherein R is an alkyl group.

16. Unsaturated polyester resin according to claim 8, further comprising an aromatic ring, a cycloaliphatic ring, or a hetero ring, which merges into a chain polymer under the influence of heat, light or ionizing radiation.

* * * * *